United States Patent
Kelly

[11] Patent Number: 6,021,919
[45] Date of Patent: Feb. 8, 2000

[54] DISPENSER FOR SANITARY GLOVES

[76] Inventor: Kevin J. Kelly, 203 S. Nutwood, Anaheim, Calif. 92804

[21] Appl. No.: 08/783,273

[22] Filed: Jan. 15, 1997

Related U.S. Application Data

[60] Provisional application No. 60/009,981, Jan. 16, 1996.

[51] Int. Cl.[7] .................................................. B65H 1/00
[52] U.S. Cl. ........................ 221/25; 221/155; 221/197; 221/281; 221/303
[58] Field of Search .............................. 221/25, 70, 155, 221/197, 281, 282, 287, 303

[56] References Cited

U.S. PATENT DOCUMENTS

| | | | |
|---|---|---|---|
| 1,208,701 | 12/1916 | Trenner | 221/25 |
| 2,587,928 | 3/1952 | Tuck et al. | 221/25 |
| 2,758,710 | 8/1956 | Arens | 221/25 |
| 2,989,212 | 6/1961 | Ekenstam et al. | 221/25 |
| 3,324,754 | 6/1967 | Peavy | 221/25 |
| 3,362,578 | 1/1968 | Spencer | 221/25 |
| 3,958,768 | 5/1976 | Fairbanks | 221/25 |
| 4,537,330 | 8/1985 | Gelbard | 221/26 |
| 4,566,606 | 1/1986 | Kling | 221/25 |
| 4,583,642 | 4/1986 | Blythe et al. | 221/303 |
| 4,844,293 | 7/1989 | McLaughlin | 221/34 |
| 4,909,413 | 3/1990 | McCutcheon | 221/25 |
| 4,993,586 | 2/1991 | Taulbee et al. | 221/25 |
| 4,993,589 | 2/1991 | McLaughlin | 221/33 |
| 5,088,620 | 2/1992 | Kelliher et al. | 221/59 |
| 5,096,089 | 3/1992 | McLaughlin | 221/26 |
| 5,119,969 | 6/1992 | Haber | 221/25 |
| 5,358,140 | 10/1994 | Pellegrino | 221/25 |

*Primary Examiner*—Christopher P. Ellis
*Assistant Examiner*—Douglas Hess
*Attorney, Agent, or Firm*—Cleveland R. Williams

[57] ABSTRACT

The present invention relates to an improved dispenser for sanitary gloves. The dispenser comprises a rectangular enclosure having a top, bottom, left and right side walls, front and back, for receiving individually packaged sanitary gloves. The front is permanently joined to the top, bottom, left and back, while the right side wall is pivotally attached to the bottom wall. The front contains an opening near the top for dispensing the sanitary gloves one at a time. A window near the bottom portion of the front is used to visually inspect the quantity of gloves remaining in the dispenser at any given time.

8 Claims, 3 Drawing Sheets

DISPENSER FOR SANITARY GLOVES

This application claims benefit under 35 U.S.C. Paragraph 119(e) of provisional application Ser. No. 60/009,981 filed on Jan. 16, 1996.

BACKGROUND FOR THE INVENTION

1. Field of the Invention

This invention relates to a dispenser for sanitary gloves in general and to a dispenser for individual packaged, sanitary gloves in individual sanitary environments in particular.

Due to the increasing seriousness of present day diseases, such as acquired immune deficiency, where the disease is acquired by contact with the body fluids of infected individuals, it is of the utmost importance for health workers and other individuals who come into close contact with a wide variety of individuals in a professional capacity, to protect themselves and prevent the spread of disease to others.

One method of protection against the spread of disease is to use a separate pair or disposable sanitary gloves for each individual contacted in a professional capacity by health workers and other professionals.

In the past sanitary gloves have been dispensed to professionals from a cardboard of similar box, wherein the gloves are randomly selected from a "pile" of gloves which are not individually protected from being cross-contaminated when someone reaches into the box to select a pair of gloves for use.

The present invention solves this problem by providing a dispenser which dispenses individual gloves which are contained in individual sanitary environments.

2. Description of the Prior Art

Several types of dispensers have been used in the past to dispense towels, gloves, sterile swabs and the like.

For example, U.S. Pat. No. 3,107,782 to Jaroff et al relates to a dispensing package for sterile swabs. The dispenser is constructed from a suitable box material such as cardboard, heavy paper of the like which contains an insert made of the same material. Surgical swabs are packaged in separate and individual swab containers. The swabs are dispensed through the top of the dispenser.

U.S. Pat. No. 2,153,278 to Shelley discloses a dispensing holder for paper towels which facilitates the loading of the holder with a pack of towels and their removal one by one as desired. The device consists of a towel dispensing holder containing a casing open at the front to receive a perforated pack of towels; supporting means for the pack includes a horizontal supporting bar, a pusher for said towels extending transversely across the interior of the casing and a delivery opening in front of the casing for dispensing the towels. The towels are removed from the dispenser by tearing them from the supporting member.

U.S. Pat. No. 2,341,119 to Rost discloses a paper towel dispenser which is described as constructed to provide for the ready removal of a single towel from the package. The device consists of a tab carried by each sheet of towel and connected by an easily severed bottom portion to an overlying sheet, therein the tab on an underlying sheet in the package will be raised to a position to be readily grasped and the top sheet is torn from the pack.

U.S. Pat. No. 4,537,330 to Gelbard relates to a dispenser for plastic bags which consist of two side panels, top and bottom panels and a back panel forming a rigid container. The front panel is hingedly attached to the bottom panel for opening and closing the dispenser. The dispenser contains a U-shaped hanger which supports the plastic bags. The bags are dispensed through an opening in the front of the dispenser near the bottom of said dispenser by tearing a perforated section of the bindings of pads of the plastic bags.

U.S. Pat. No. 4,844,293 to Mclaughlin describes a dispensing apparatus for disposable, thin plastic gloves wherein the gloves may be retrieved by the user one at a time. The device consists of a box like, rectangular type enclosure for housing a removably mounted packet containing a plurality of gloves. The dispenser contains a front window and a removable top cover or cap. The gloves are biasly urged toward the front window of the dispenser using a leaf spring arrangement to present the outermost glove to the user.

U.S. Pat. No. 4,863,084 to Nabozny relates to a hip holster for gloves. The device consists of a portable, disposable gloves dispensing system which can be worn by the user. In particular, the device has a support and attachment plate member to which are securely attached a plurality of gloves. Optionally, the device contains a frangible line of detachment, waist strap members, apertures for attachment to the user's belt and a stabilizer band.

U.S. Pat. No. 5,088,620 to Kellihur et al discloses a dispenser for gloves consisting of a tubular body having a first end and a second end and having a spring disposed therein. The spring is attached to a movable disc shaped member. A flexible nipple shaped element having a first end and a second end is secured to the disc shaped member at the first end and secures a plurality of gloves therein. A top element slidably fits over the top of the tubular body and has an opening therein and a diaphragm element having an aperture therein. The spring urges the disc member against the nipple shaped member containing the gloves, allowing for removal of one glove at a time from the device.

U.S. Pat. No. 5,096,089 to McLaughlin describes a dispensing device for thin, disposable plastic gloves which allows for the removal of gloves one at a time from the device. The dispensing apparatus consists of a rectangular shaped enclosure for housing a removably mounted packet containing a plurality of gloves. The gloves are arranged in closely spaced, parallel relationship to one another for removal one at a time through an opening in the walls of said enclosure. The packet of gloves includes a mounting strip which extends across the upper wrist portion of the stack of gloves and is fixed to each glove above the tear line. Each glove is removed by exerting a downward force through the opening of the enclosure.

As can readily be determined from the foregoing, there is an ongoing research effort and a need to develop and produce new and novel dispensing devices for gloves and the like.

SUMMARY OF THE INVENTION

The present invention relates to sanitary disposable gloves dispensers generally, and particularly to an improved sanitary glove dispenser and sanitary gloves enclosed in individual sanitary packages, which promotes more reliable and efficient dispensing of one pair of gloves at a time while protecting the sanitary environment of each of said pairs of gloves during storage and dispensing of the same.

The invention relates to a dispenser for sanitary gloves comprising a rectangular enclosure having a top, bottom and side walls, for receiving individually packaged sanitary gloves. The front side wall is permanently joined to the top, bottom, left and back side walls; the right side wall is pivotally attached to the bottom wall and connectably attaches to the top wall.

The front wall contains an opening at the top portion for dispensing sanitary gloves and a window near the bottom portion. The rectangular enclosure defines a space for receiving individually packaged sanitary gloves, each package folded one upon the other and attached to each other via serrated tear strips.

DETAILED DESCRIPTION OF THE INVENTION

The present invention resides in a device and method for dispensing sanitary gloves without the probability of contaminating said gloves.

Particularly, the invention comprises a generally rectangular shaped dispenser containing an opening near the top, located at the front of the dispenser with an eye gauge located near the bottom portion of the front of said dispenser. One side of the dispenser opens pivotally to receive a plurality of sanitary gloves, each pair of sanitary gloves is individually contained in separate sterilized packages which are removably attached to a plurality of separate sterilized packages containing said gloves.

The separate sterilized packages of sanitary gloves are removably attached one to the other and systematically stacked upon each other. One method of maintaining the sterile environment for the gloves is to vacuum wrap the gloves in a controlled sterile environment.

The stacked packages containing the sanitary gloves are placed into the dispenser and the top package is inserted through the opening at the top of the dispenser.

When an individual wishes to use a pair of sanitary gloves, he pulls the glove through the dispenser opening and tears the package from the connecting package at the designated portion of said package which prevents contamination of said gloves. Next, the sanitary package containing the gloves is torn open and the gloves are placed on the hands of the user.

It should be noted that gravity maintains the plurality of packages containing said gloves in stacked formation until the gloves are ready for use.

The invention comprises a dispenser for sanitary gloves wherein the sanitary gloves are individually packaged in a sanitary environment.

Figure 1:
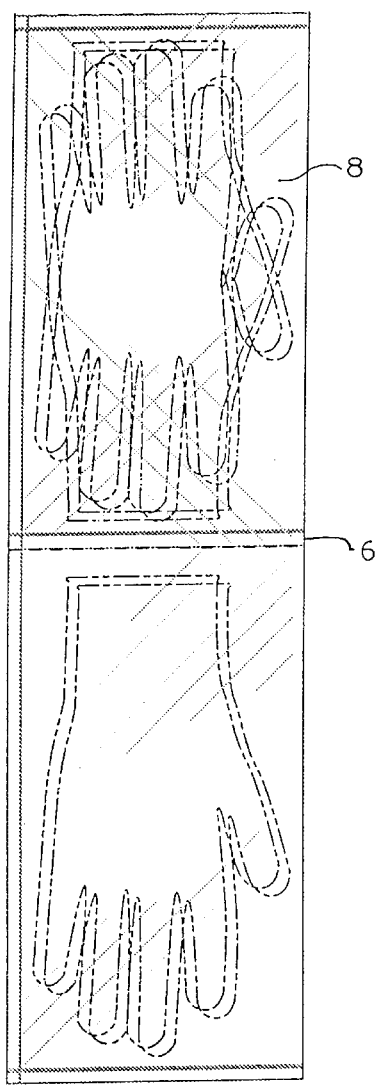
FIG. 1 is a top view of individually packaged sanitary gloves showing one package of gloves detached from the other gloves.

FIG. 1 is a top view of sanitary gloves (one pair) 4 enclosed in a sanitary environment 2, which normally consist of either clear plastic or a polymer.

Perforated, tear strip 6 attaches a plurality of clear plastic or polymer sealed pouches each of which contain a pair of sanitary gloves 4.

Figure 2:
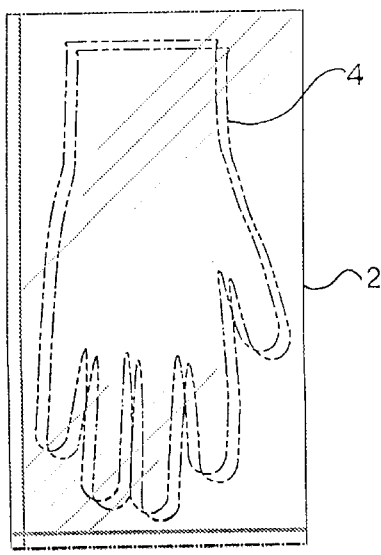
FIG. 2 is a front view of a dispenser showing the front wall along line 3—3, and the side wall in the open position along line 4—4.
Figure 2:
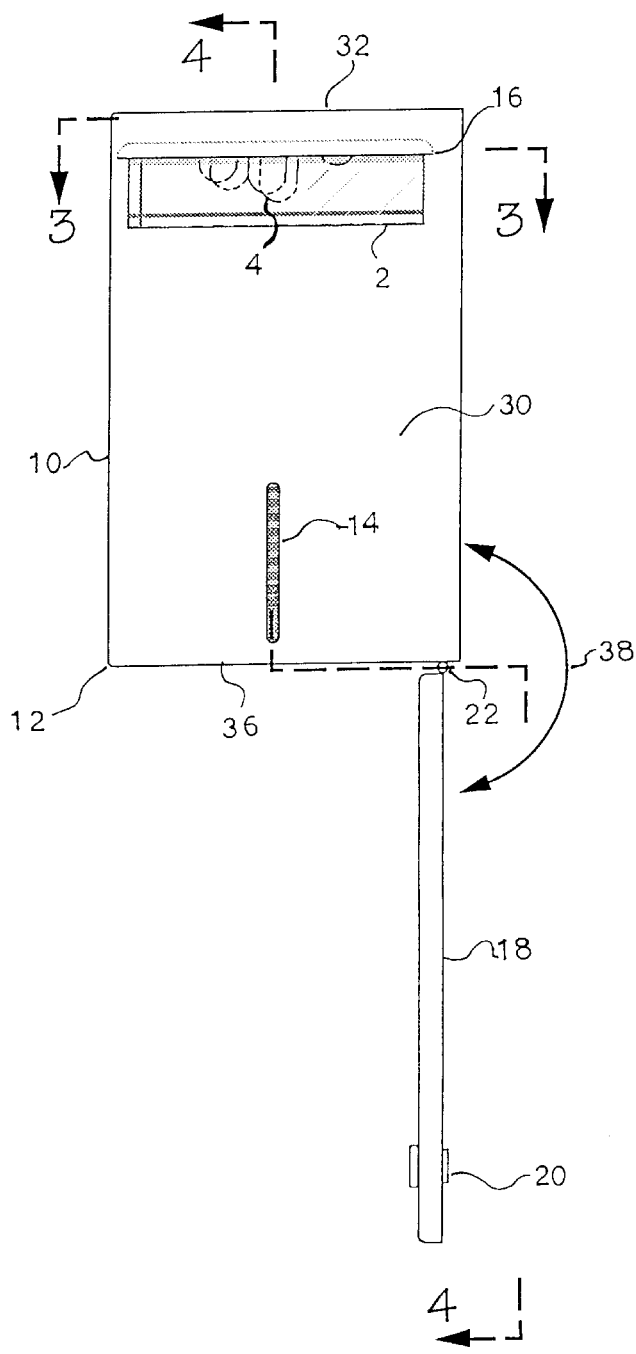

FIG. 2 is a front view of rectangular shaped dispenser 12 showing top 32, bottom 36, left side 10, right door 18 and front 30. Right door 18 is hingably attached to bottom 36 by pivot means 22. Right door 18 pivots in the direction of angle 38. Latch means 20 is attached to right door 18 near the top portion thereof.

The front 30 of dispenser 12 contains sight window 14 near the bottom portion thereof. Opening 16 located near the top portion of front 30 allows for dispensing package 2 containing sanitary gloves 4.

Figure 3:
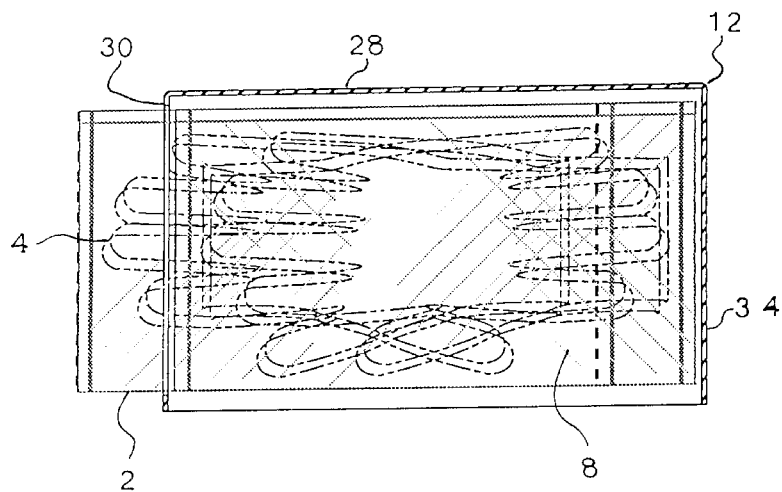
FIG. 3 is a top view of individual packages of sanitary gloves in a stacked position.

FIG. 3 is a top, cut-away view of dispenser 12 showing front 30, left side 28, back side 34 and right door 18. Stacked inside dispenser 12 is a plurality of sanitary sealed pouches 8 yieldably attached to each other and one single pouch 2 emerging from the front of said dispenser.

Figure 4:
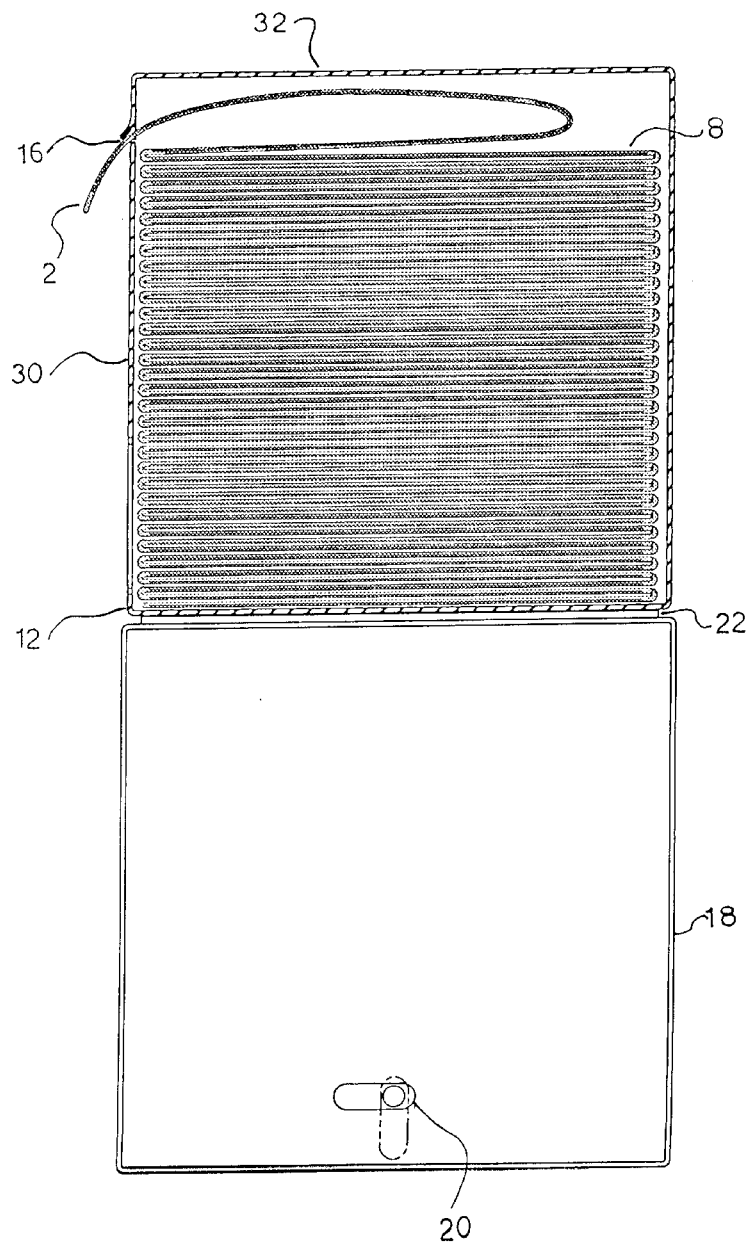
FIG. 4 is a side view of the dispenser with the side door open and showing stacked, individual packages of sanitary gloves in the dispensing position.

FIG. 4 is a side view of dispenser 12 showing the top 32, back 34, door 18 is in the open position, containing latch 20 and hinge means 22. A plurality of sealed pouches 8 containing sanitary gloves are contained in the cavity of dispenser 12 in a stacked position. Single sanitary pouch 2 still removably connected to the plurality of pouches 8 is emerging from opening 16 of the front 30 of dispenser 12.

Figure 5:
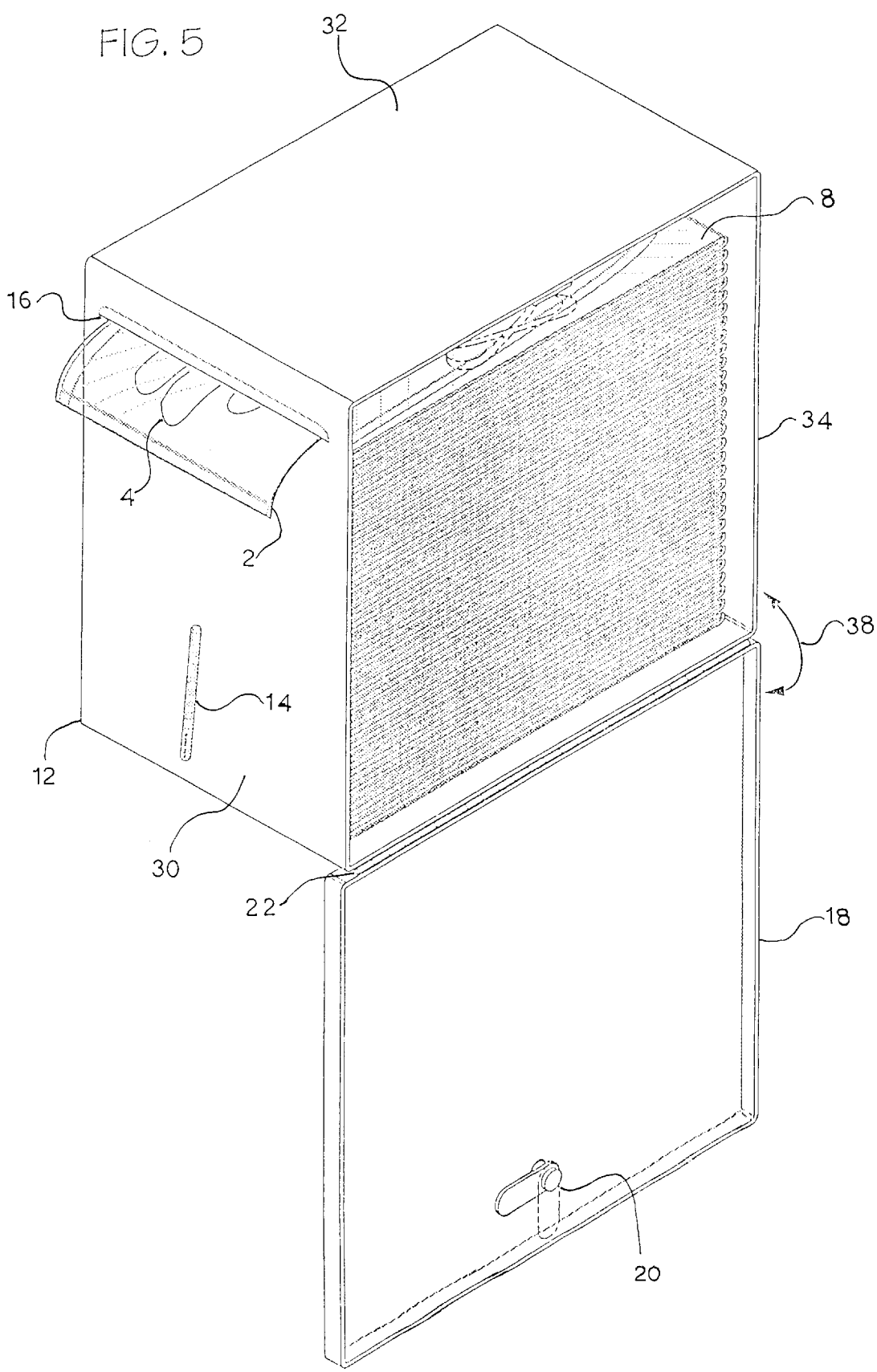
FIG. 5 is a frontal perspective view of the dispenser and stacked sanitary gloves in a dispensing position.

FIG. 5 is a perspective view of dispenser 12 with right door 18 in an open position depicting the stacked relationship of the plurality of pouches 8, containing individual pairs of sanitary gloves 4. Otherwise the various elements of this view are the same as those in FIGS. 2 and 4.

I claim:

1. A dispenser for individually packaged, sanitary gloves in individual sanitary environments which comprises a generally rectangular shaped dispenser containing a front, back, right and left sides, top, bottom and interior cavity; and a plurality of individually packaged sanitary gloves contained in separate sterilized packages which are removably attached to a plurality of separate sterilized packages containing said gloves located in said interior cavity, wherein the front contains a horizontal, elongated opening near the top portion thereof and a vertical elongated cylindrical opening near the bottom portion thereof, and wherein gravity maintains the plurality of packages containing said sanitized gloves in stacked formation in the rectangular shaped enclosure until the gloves are ready for use; said right side of the dispenser being pivotally attached to the bottom and is connectable attached to the top thereof.

2. The dispenser for the individually packaged, sanitary gloves of claim 1, wherein each pair of sanitized gloves is individually contained in separate sterilized packages which are removably attached to a plurality of separate sterilized packages containing said gloves.

3. The dispenser for the individually packaged, sanitary gloves of claim 1, wherein the plurality of separately packaged sanitary gloves are stacked in the interior cavity of the rectangular shaped dispenser and the top package is inserted through the opening near the top portion of the front of said dispenser.

4. A dispenser for sanitized gloves which comprises a rectangular shaped enclosure having a top, bottom, front, back and right and left sides, said enclosure defining a space; and a plurality of individually packaged sanitized gloves, each package folded one upon the other and attached to each other via serrated tear strips located in said enclosure, wherein the front contains a horizontal, elongated opening near the top portion thereof and a vertical elongated cylindrical opening near the bottom portion thereof, and wherein gravity maintains the plurality of packages containing said sanitized gloves in stacked formation in the rectangular shaped enclosure until the gloves are ready for use; said right side of the dispenser being pivotally attached to the bottom and is connectably attached to the top thereof.

5. The dispenser for the sanitized gloves described in claim 4, wherein the front of the rectangular shaped enclosure is permanently joined to the top, bottom, back and left side and the right side and connectably attaches to the top.

6. The dispenser for the sanitized gloves of claim 4 wherein the horizontal elongated opening near the top portion is for dispensing sanitized gloves and the vertical opening is used as a sight window near the bottom portion thereof.

7. The dispenser for the sanitized gloves of claim 4, wherein the sanitized gloves are individually packaged in a sanitary environment.

8. The dispenser for the sanitized gloves of claim 7, where the sanitized gloves are individually vacuum wrapped in a sanitary environment.

* * * * *